United States Patent [19]

Bradford

[11] Patent Number: Plant 5,454

[45] Date of Patent: Apr. 30, 1985

[54] NECTARINE TREE (MAY DIAMOND)

[76] Inventor: Norman G. Bradford, 11875 E. Savana Rd., Le Grand, Calif. 95333

[21] Appl. No.: 535,263

[22] Filed: Sep. 23, 1983

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Vergil L. Gerard

[57] ABSTRACT

The present invention relates to a nectarine tree and more particularly to a new and distinct variety broadly characterized by a medium size, vigorous, hardy, productive and regular bearing tree. The fruit matures under the ecological conditions described approximately the third week in June, with first picking on June 13, 1983. The fruit is of medium size, very firm and crisp when ripe making excellent quality for keeping and shipping, and has an attractive dark red skin and a sweet, acidic flavor.

1 Drawing Figure

BACKGROUND OF THE VARIETY

The instant variety most nearly resembles the May Grand nectarine (U.S. Plant Pat. No. 2,794), ripening at the same time as May Grand but is distinguished therefrom and an improvement thereon by coloring earlier and thereby having a full red color at shipping time, being somewhat larger, and much firmer and crisper.

The instant variety was discovered by me at Bradford Farms in Merced County (San Joaquin Valley), Calif., as the result of open pollination of a first generation seedling of a Red Diamond nectarine (U.S. Plant Pat. No. 3,165). I asexually reproduced the resulting plant by budding and grafting, and such reproduction of plant and fruit characteristics were true to the original plant in all respects.

DRAWING

The accompanying photograph shows the characteristics of a whole fruit in skin color and form, a characteristic fruit divided on its suture plane showing the flesh and stone cavity, and a characteristic stone and leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the stage of firm, but over ripe, on June 29, 1983. All color plate identifications are by reference to Dictionary of Color, 1950 (2d ed) by Maerz and Paul.

TREE

General: Of medium size, hardy, vigorous and dense, of medium spreading and vase shape, with desired shape and density determined by pruning. Very productive and regular bearing.

TRUNK

General: Of medium diameter, grayish-brown, medium shaggy; numerous orange-tan lenticles $\frac{1}{4}''$ to $\frac{3}{8}''$ in length.

BRANCHES

General: Of medium size and surface texture; second year and older growth is brown in color, newer growth brown on dorsal side and brown with some green on ventral side. Numerous tan, medium size lenticles, $\frac{1}{8}''$ to 3/16" in length.

LEAVES

Size: Average length, $5\frac{1}{2}''$, average width, $1\frac{1}{2}''$.

Form: Lanceolate.

Base: Broadly acute.

Apex: Acutely pointed.

Margin: Crenate.

Veins: Pinnately net veined.

Petiole:

*Medium.*—Average length, 5/16", medium thickness.

Glands: Averaging two, sometimes four, alternatingly opposed, reniform, green glands on petiole and base of leaf.

Stipules: Two per leaf, $\frac{1}{8}''$ to $\frac{1}{4}''$ in length.

Leaf buds: Pointed.

FLOWERS

Buds: Hardy, medium length and diameter; pointed, free.

Flowers: Small, medium bloom date compared with other varieties. Dark pink in color. Some anthers protrude through bud before flower opens.

FRUIT

Maturity when described: Hard, but over ripe, on June 29, 1983.

Size: Uniform, medium size; axial diameter, $2\frac{3}{8}''$, transverse in suture plane, $2\frac{1}{2}''$.

Form: Uniform, symmetrical; globose to slightly oblong. Longitudinal section, elliptical, slightly oblong; transverse through diameter, round.

Suture: Shallow, extending from base to beyond apex with only an inconspicuous line on dorsal side. Slight depression beyond pistil point.

Ventral surface: Slightly rounded, lipped slightly throughout on both sides, lips equal.

Cavity: Rounded with suture showing on both sides. $\frac{3}{8}''$ in depth, $\frac{1}{2}''$ in breadth.

Base: Truncate.

Apex: Truncate.
Pistil point: Slight depression surrounding a small pistil point.
Stem: Medium size; length, $\frac{1}{4}''$, width 3/16".
Skin:
*General.*—Medium thickness, medium tender. Tenacious to flesh. Tendency to crack is very slight.
Skin color: Dark red (Garnet 7-J-6), with some yellow speckling at apex.
Flesh:
*Amygdalin.*—Moderate.
*Juice.*—Rich and abundant.
*Texture.*—Firm, very crisp.
*Flesh fibres.*—Abundant; fine, tender.
*Flavor.*—Acid.
*Aroma.*—Pronounced.
*Ripens.*—Evenly.
*Eating quality.*—Acidic; very good.
*Firmness.*—Extremely firm and crisp.
Flesh color: Yellow (Corn 10-J-5) with slight amount of red next to skin and stone; surface of pit cavity yellow (10-K-5) with few yellow fibres.

STONE

Tenacity: Semi-free at shipping ripe, free at eating ripe.
Form: Elliptical.
Base: Straight.
Apex: Acute, side equal and slightly flattened.
Surface: Irregularly furrowed near apex, pitted from base to above midpoint.

Ridges: Rounded.
Size: Length, $1\frac{1}{4}''$, width, 11/16"; thickness, $\frac{1}{2}''$.
Color: Harvest (12-H-9) — orange-tan.
Thickness of pit wall: $\frac{1}{4}''$.
Tendency to split: Slight.
Kernel: Oval form, sweet, viable. Width, $\frac{1}{2}''$, length, $\frac{3}{4}''$, thickness, $\frac{1}{4}''$. Light yellow pellicle. No amygdalin.

RESISTANCE TO INSECTS AND DISEASE

No unusual susceptibilities noted.

USE

Local market, long distance shipping. Excellent keeping quality and shipping quality.

The nectarine tree and its fruit herein described may vary in slight detail due to climatic and soil conditions under which the variety may be grown.

I claim:

1. A new and distinct variety of semi-freestone nectarine tree, substantially as illustrated and described, which most closely resembles May Grand Nectarine (U.S. Plant Pat. No. 4,791) and has fruit which ripens at the same time, but which is distinguished therefrom and is an improvement thereon in that its fruit colors earlier during ripening, and when shipping ripe has a fuller red color and is much firmer than May Grand and has a more acidic nectarine taste, and in that the pollen anthers frequently protrude out of the flower bud before the flower opens.

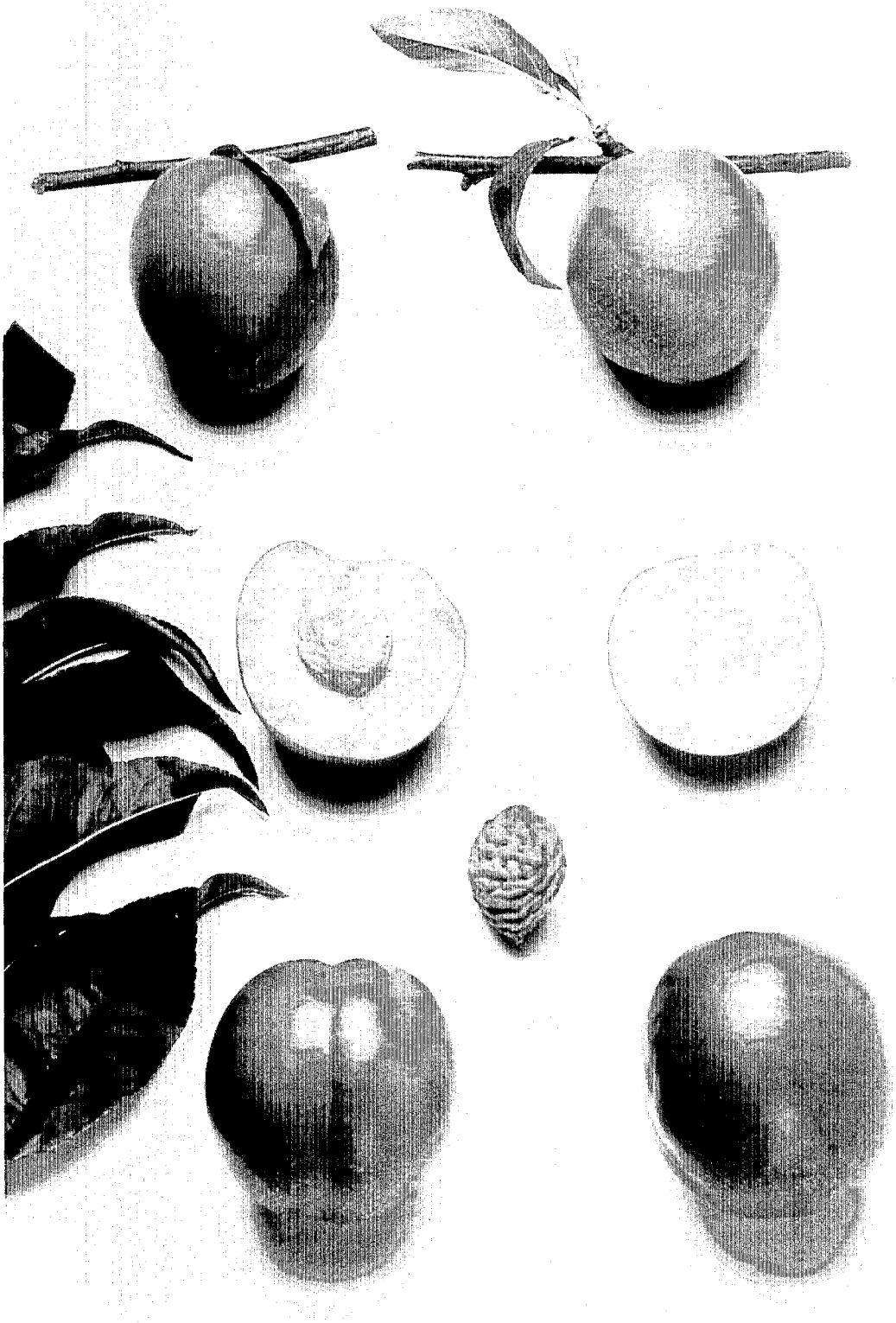

* * * * *